United States Patent [19]

Covitz

[11] Patent Number: 4,625,717
[45] Date of Patent: Dec. 2, 1986

[54] INTEROSSEOUS WIRING SYSTEM

[76] Inventor: William M. Covitz, 36 Rockledge Rd., Newton, Mass. 02161

[21] Appl. No.: 745,063

[22] Filed: Jun. 17, 1985

[51] Int. Cl.⁴ ............................................. A61F 5/04
[52] U.S. Cl. ................................. 128/92; 128/92VK; 128/303 R; 128/92 YD; 92V
[58] Field of Search ................. 128/92 E, 92 R, 92 A, 128/69, 303 R

[56] References Cited

U.S. PATENT DOCUMENTS

| | | | |
|---|---|---|---|
| 3,209,422 | 10/1965 | Dritz | 24/150 |
| 4,527,554 | 7/1985 | Klein | 128/92 E |
| 4,531,517 | 7/1985 | Forte et al. | 128/92 R |
| 4,557,259 | 12/1985 | Wu | 128/92 E |
| 4,570,618 | 2/1986 | Wu | 128/92 E |

FOREIGN PATENT DOCUMENTS

| | | | |
|---|---|---|---|
| 1958429 | 7/1971 | Fed. Rep. of Germany | 128/92 E |
| 3305267 | 8/1984 | Fed. Rep. of Germany | 128/92 E |
| 929088 | 5/1982 | U.S.S.R. | 128/92 E |

OTHER PUBLICATIONS

Downs Bros. & Meyer & Phelps Ltd., p. G67 of "Orthopaedic Catalog" Catalog date unknown.

Primary Examiner—Gene Mancene
Assistant Examiner—C. W. Shedd
Attorney, Agent, or Firm—Schiller & Pandiscio

[57] ABSTRACT

An interosseous wiring system comprising a wire having an enlargement formed on the leading end thereof and a threading tool, said threading tool having means for attaching said enlargement to the front tip of said tool, in order that said wire may be threaded through a hole by passing the front tip of said tool through said hole, attaching the wire to said tool, and thereinafter withdrawing said front tip of said tool back through said hole, thereby carrying the leading end of said wire back through said hole.

5 Claims, 7 Drawing Figures

INTEROSSEOUS WIRING SYSTEM

FIELD OF THE INVENTION

This invention relates to surgical apparatus in general, and more particularly to surgical apparatus of the sort used to repair fractures in delicate bones.

BACKGROUND OF THE INVENTION

When a human bone has been fractured, the fractured portions must be properly aligned with one another so as to allow for proper healing. Sometimes proper alignment can be achieved without artificial assistance. At other times it may be necessary to stabilize the bone about the point of the fracture with special surgical apparatus. In situations where the fractured bone is fairly large, e.g. a femur, a tibia, a fibula, etc., such stabilization can be effected through a wide variety of surgical apparatus, e.g. pins, plates, etc. However, where the fractured bone is fairly small and delicate, e.g. a metacarpal, a phalanx, a metatarsal, etc., the choice of surgical apparatus is substantially more restricted. In general, a small and delicate bone can be stabilized about the point of the fracture only by wiring together the fractured portions of the bone with very fine, flexible steel wire. In such interosseous wiring, the surgeon typically first drills one or more holes through the bone on each side of the fracture line, and then threads the wire in and out of the holes and across the fracture line so as to effectively tie the fractured portions of the bone together in healing position.

Unfortunately, in the case of small bones, the surgical holes and interosseous wire must be sized as fine as possible. This presents something of a problem, inasmuch as it can be time-consuming and tiring to thread a flexible steel wire through the tiny surgical holes, a procedure roughly analagous to threading a needle. This is particularly true under the difficult operating constraints frequently imposed by the fracture site.

OBJECTS OF THE INVENTION

Accordingly, the principal object of the present invention is to provide a novel interosseous wiring system which facilitates the deployment of interosseous wire about a fracture site.

Another object of the invention is to provide a novel interosseous wiring system which is simple to use, inexpensive to manufacture, and effective in operation.

SUMMARY OF THE INVENTION

These and other objects of the invention are addressed by a novel interosseous wiring system which comprises an interosseous wire and a threading tool. The interosseous wire of the present invention is an ordinary interosseous wire, except that it has an enlargement formed on its leading end. The threading tool comprises a shaft having a side recess near its front tip, and a canal extending axially between the side recess and the tool's front tip. The recess is sized so as to be slightly larger than the enlargement formed on the leading end of the wire, and the canal is sized so as to be slightly wider than the width of the wire, yet substantially narrower than the width of the enlargement formed on the leading end of the wire, in order that the wire can be attached to the threading tool by positioning the wire's enlargement in the tool's recess and extending the trailing end of the wire out through the tool's canal and away from the tool's front tip, and then gently pulling on the trailing end of the wire in a direction away from the threading tool so that tension keeps the enlargement properly seated in the recess and the wire thereby attached to the tool.

When it is desired to use the novel interosseous wiring system to thread an interosseous wire through a hole from a first side of a bone to a second side of the same bone, i.e., as part of an interosseous wiring procedure intended to repair a fracture in the bone, the threading tool is passed through the hole from the second side of the bone to the first side, so that the threading tool's front tip thereafter resides on the first side of the bone while a trailing portion of the threading tool resides on the second side of the bone. Then the leading end of the wire is attached to the front tip of the threading tool in the manner previously described, i.e., by positioning the wire's enlargement in the tool's side recess and threading the trailing end of the wire out through the tool's canal, and then gently pulling on the trailing end of the wire in a direction away from the threading tool so that tension keeps the enlargement properly seated in the recess and the wire thereby attached to the tool. Next the tool is withdrawn back through the bone, carrying the leading end of the wire with it, until the front tip of the tool (and the leading end of the wire) emerge from the hole on the second side of the bone. Then the interosseous wire is disengaged from the threading tool by relaxing the tension on the wire and dismounting the wire's enlargement from the tool's recess.

BRIEF DESCRIPTION OF THE DRAWINGS

Still other objects and features of the present invention will be more fully disclosed or rendered obvious in the following detailed description of the preferred embodiment of the invention, which is to be considered together with the accompanying drawings wherein like figures refer to like parts and further wherein.

DETAILED DESCRIPTION OF THE PREFERRED EMBODIMENT

Figure 1:
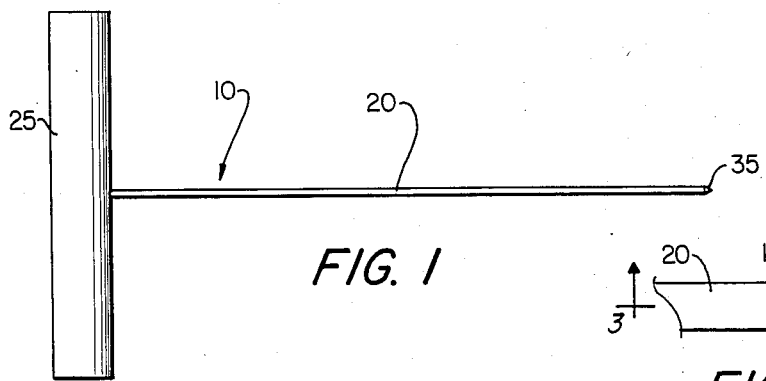
FIG. 1 is a top plan view of the threading tool.
Figure 2:
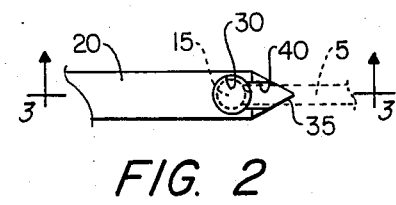
FIG. 2 is an enlarged fragmentary top plan view showing the front tip of the threading tool engaging the leading end of the interosseous wire, wherein the wire is shown in phantom.

Looking first at FIGS. 1-4, the preferred embodiment of the present invention comprises an interosseous wire 5 and a threading tool 10. Wire 5 is a wire of the sort typically used in interosseous wiring procedures, e.g. it is a flexible stainless steel wire approximately 0.38 mm in diameter, except that it has an enlargement 15 formed on its leading end. Preferably, the enlargement 15 is in the shape of a spherical ball formed integral with the leading end of the wire, and is sized so as to be substantially wider in diameter than wire 5, e.g. enlargement 15 is approximately 0.81 mm in diameter. Enlargement 15 is preferably formed on the leading end of wire 5 simply by melting and beading the end of the wire by high temperature melting.

Threading tool 10 comprises a stiff metal shaft 20 and a handle 25. Shaft 20 is circular in cross-section and is sized so as to be somewhat wider in diameter than the diameter of the wire's enlargement 15, e.g. shaft 20 is approximately 0.89 mm in diameter. Shaft 20 has a side recess 30 located adjacent its front tip 35. Recess 30 is cylindrical in shape. The diameter and depth of recess 30 both slightly exceed the diameter of the wire's enlargement 15, e.g. they are both 0.84 mm in dimension, in order that recess 30 can accommodate the wire's enlargement 15 without the enlargement protruding out of recess 30.

Figure 4:
FIG. 4 is a front end view in elevation showing the front tip of the threading tool.

Threading tool 10 also has a canal or groove 40 extending axially between recess 30 and the tool's front tip 35. Preferably, canal 40 has a U-shaped cross-section as shown in FIG. 4. Canal 40 is sized so as to have a width slightly greater than the diameter of wire 5, e.g. 0.40 mm, and a depth slightly greater than the radius of the wire's enlargement 15, e.g. 0.43 mm, in order that canal 40 can accommodate the trailing end of wire 5 when the wire's enlargement 15 is seated in the tool's recess 30. It is to be appreciated that canal 40 is sized so that it has a width substantially smaller than the diameter of the wire's enlargement 15, so as to prevent the enlargement from passing out of recess 30 through canal 40. It is also to be appreciated that on account of the foregoing construction, wire 5 can be attached to threading tool 10 by positioning the wire's enlargement 15 in the threading tool's side recess 30 and extending the trailing end of wire 5 out through the tool's canal 40 and away from the tool's front tip, and then gently pulling on the trailing end of wire 5 in a direction away from the threading tool so that tension keeps the wire's enlargement 15 properly seated in recess 30 and the wire thereby attached to the tool.

Figure 5:
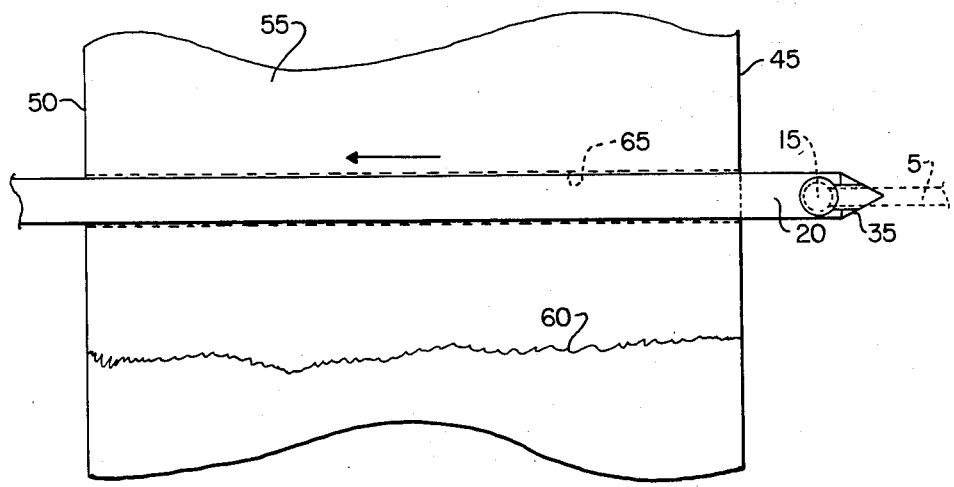
FIG. 5 is a top plan view showing the threading tool about to be withdrawn back through a bone.

Looking next at FIG. 5, the interosseous wiring system is adapted to be utilized as follows. When it is desired to pass wire 5 from a first side 45 to a second side 50 of a bone 55, e.g. as part of an interosseous wiring procedure intended to repair a fracture 60, a hole 65 is first drilled through the bone. Hole 65 is sized so as to be slightly larger in diameter than the diameter of the threading tool's shaft 20, e.g. hole 65 is 1.10 mm in diameter. Then the threading tool's front tip 35 is passed through hole 65, from the bone's second side 50 to its first side 45, so that the tool's front tip 35 thereafter resides on the first side of the bone while a trailing portion of the tool's shaft resides on the second side of the bone. Next wire 5 is attached to the threading tool in the manner previously described, i.e., by positioning the wire's enlargement 15 in the threading tool's recess 30 and passing the trailing end of the wire out through the tool's canal 40, and then gently pulling on the free end of the wire so as to put the wire into tension and thereby maintain the wire's enlargement properly seated in the tool's recess. Then the tool is withdrawn back through bone 55, carrying the leading end of wire 5 with it, until the tool's front tip 35 (and the leading end of wire 5) resides on the second side 50 of the bone. Wire 5 is then released from the threading tool by first relaxing the tension placed on the trailing end of the wire, and then dismounting the wire's enlargement 15 from the tool's side recess 30 and the wire's body from the tool's canal 40. It will, of course, be appreciated that it will generally be easiest to position the wire's enlargement 15 in the threading tool's recess 30 and the wire's body in the tool's canal 40 when the threading tool is oriented so that its recess 30 and canal 40 are located at the "top" of the shaft, i.e., in the position shown in FIGS. 2–5, whereby gravity will assist loading of the wire into recess 30 and canal 40.

Figure 6:
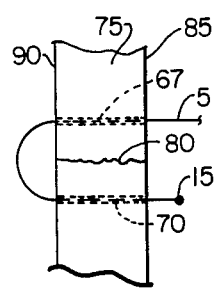
FIGS. 6 and 7 are top plan views showing various ways in which the interosseous wire may be deployed about a fracture in a bone.

It is to be appreciated that the desired interosseous wiring of a fractured bone can be accomplished simply by repeating the foregoing procedure as required. Thus, for example, if it should be desired to create a so-called "tension band" with interosseous wiring (FIG. 6), a pair of parallel holes 67 and 70 are first drilled into bone 75 on opposite sides of a fracture 80, so that each hole connects a first side 85 of the bone with a second side 90 of the bone. Then the leading tip of the threading tool is passed through hole 67 from the bone's second side 90 to its first side 85, where it is attached to the leading end of wire 5 in the manner previously described. Next the tool is withdrawn back through hole 67, carrying the leading end of the wire with it, until the tool's front tip 35 (and the leading end of wire 5) resides on the second side 90 of the bone. Then the wire is released from the threading tool in the manner previously described. Next the front tip of the threading tool is passed through hole 70 from the bone's first side 85 to its second side 90, where it is once again attached to the leading end of the wire in the manner previously described. Then the threading tool is withdrawn back through hole 70, carrying the leading end of the wire with it, until the tool's front tip 35 (and the leading end of wire 5) resides on the first side 85 of the bone. Then the interosseous wire is released from the threading tool in the manner previously described. The threaded wire can then be secured under tension so as to form the so-called "tension band" about the fracture.

Figure 7:
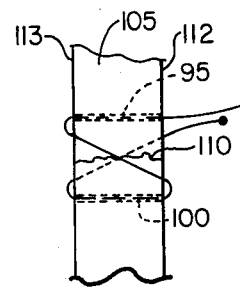
Figure 3:
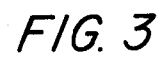
FIG. 3 is a sectional view taken along line 3—3 of FIG. 2.

Alternatively, if it is desired to utilize the interosseous wiring system to form a so-called "figure eight fixation" (FIG. 7), a pair of parallel holes 95 and 100 are first drilled through bone 105 on either side of fracture 110, so that each hole connects a first side 112 of the bone with a second side 113 of the bone. Then wire 5 is threaded through hole 95 (from side 112 to side 113) with threading tool 10 in the manner previously described. Next the wire is drawn diagonally across the exterior of bone 105 so that its lead end is returned to first side 112 of the bone. Then the wire is threaded through hole 100 with threading tool 10 in the manner previously described. Next the wire is drawn diagonally across the exterior of bone 105 so that its lead end is returned to first side 112 of the bone. Finally, the threaded wire is secured under tension, so as to form the so-called "figure eight fixation" about the fracture.

MODIFICATION OF THE PREFERRED EMBODIMENT

It is, of course, possible to modify the preferred embodiment described and illustrated above without departing from the scope of the present invention.

Thus, for example, the shape of enlargement 15 formed on the leading end of wire 5 and the shape of recess 30 formed on the side of shaft 20 could be modified from the shapes previously described, e.g. enlargement 15 could be formed in the shape of a cylinder rather than in the shape of a sphere (and recess 30 left unaltered), or enlargement 15 could be formed in the shape of a square cube and the threading tool's side recess 30 could be formed in the corresponding shape of a square hole, or enlargement 15 could be formed in the shape of a rod set perpendicular to wire 5 (i.e., so as to form a "T") and recess 30 could be formed in the shape of a slot set perpendicular to canal 40 (i.e., so as to form a corresponding "T").

Alternately, the various dimensions of wire 5, enlargement 15, shaft 20, recess 30, canal 40, etc. could be varied somewhat from the dimensions provided above.

These and other changes of their type will be obvious to persons skilled in the art, and are considered to be within the scope of the present invention.

What I claim is:

1. An interosseous wiring system comprising:
   (a) a wire having an enlargement formed at one end thereof; and
   (b) a threading tool for threading said wire through a hole, said threading tool comprising a shaft having a front end terminating in a tip, a side recess formed in said shaft adjacent said front end, and a canal extending axially from said side recess to said tip, said side recess being sized so as to accommodate said enlargement, and said canal being sized so as to accommodate the body of said wire but not said enlargement, whereby said wire may be attached to said threading tool by positioning said enlargement in said side recess and said wire in said canal.

2. An interosseous wiring system according to claim 1 wherein said enlargement comprises a spherical ball formed integral with said wire.

3. An interosseous wiring system according to claim 1 wherein said side recess comprises a cylindrical blind hole formed in said shaft.

4. An interosseous wiring system according to claim 1 wherein said threading tool comprises a handle affixed to a rear end of said shaft.

5. A surgical threading tool for threading a wire of the type having an enlargement on its leading end through a hole in a bone, said threading tool comprising a shaft having a side recess adjacent one end thereof, and a canal extending from said side recess to said one end of said shaft, said recess being sized so as to accommodate said enlargement formed on said leading end of said wire, and said canal being sized so as to accommodate said wire but not said enlargement, whereby said wire may be attached to said threading tool by positioning said enlargement in said side recess and threading said wire into said canal.

* * * * *